US012571018B2

(12) United States Patent (10) Patent No.: US 12,571,018 B2
Matsuo et al. (45) Date of Patent: Mar. 10, 2026

(54) METHOD FOR PRODUCING COMPOSITION CONTAINING POLYPEPTIDE WITH SUPPRESSED COLORING

(71) Applicant: Chugai Seiyaku Kabushiki Kaisha, Tokyo (JP)

(72) Inventors: Takahiro Matsuo, Tokyo (JP); Masao Mori, Tokyo (JP); Atsushi Kunimune, Tokyo (JP)

(73) Assignee: CHUGAI SEIYAKU KABUSHIKI KAISHA, Tokyo (JP)

( * ) Notice: Subject to any disclaimer, the term of this patent is extended or adjusted under 35 U.S.C. 154(b) by 696 days.

(21) Appl. No.: 17/795,075

(22) PCT Filed: Jan. 29, 2021

(86) PCT No.: PCT/JP2021/003215
§ 371 (c)(1),
(2) Date: Jul. 25, 2022

(87) PCT Pub. No.: WO2021/153723
PCT Pub. Date: Aug. 5, 2021

(65) Prior Publication Data
US 2023/0093028 A1 Mar. 23, 2023

(30) Foreign Application Priority Data

Jan. 31, 2020 (JP) ................................. 2020-014739

(51) Int. Cl.
*C12P 21/02* (2006.01)
*C07K 16/00* (2006.01)
*C07K 16/22* (2006.01)
*C07K 16/24* (2006.01)
*C07K 16/36* (2006.01)
*C12N 5/00* (2006.01)
*C12N 5/10* (2006.01)
*C12N 15/85* (2006.01)

(52) U.S. Cl.
CPC .............. *C12P 21/02* (2013.01); *C07K 16/00* (2013.01); *C07K 16/22* (2013.01); *C07K 16/244* (2013.01); *C07K 16/36* (2013.01); *C12N 5/0031* (2013.01); *C12N 5/10* (2013.01); *C12N 15/85* (2013.01); *C07K 2317/14* (2013.01); *C07K 2317/52* (2013.01); *C12N 2500/38* (2013.01); *C12N 2510/02* (2013.01); *C12N 2511/00* (2013.01)

(58) Field of Classification Search
None
See application file for complete search history.

(56) References Cited

U.S. PATENT DOCUMENTS

| | | | |
|---|---|---|---|
| 2013/0281355 A1 | 10/2013 | Vijayasankaran et al. | |
| 2015/0079632 A1* | 3/2015 | Jost | C12P 21/02 |
| | | | 435/431 |
| 2016/0200807 A1 | 7/2016 | Ruike et al. | |

FOREIGN PATENT DOCUMENTS

| | | |
|---|---|---|
| CN | 101724074 A | 6/2010 |
| CN | 109311969 A | 2/2019 |
| JP | 2006212033 A | 8/2006 |
| JP | 2015514408 A | 5/2015 |
| JP | 2015515281 A | 5/2015 |
| JP | 2017535244 A | 11/2017 |
| WO | WO2017173359 A2 | 10/2017 |
| WO | WO2017217525 A1 | 12/2017 |
| WO | WO2018208743 A1 | 11/2018 |

OTHER PUBLICATIONS

Du et al. Vitamin B12 association with mAbs: Mechanism and potential mitigation strategies Biotech. and Bioeng. 115(4):900-909, 2018.*
Conrad. https://www.sigmaaldrich.com/US/en/technical-documents/technical-article/cell-culture-and-cell-culture-analysis/mammalian-cell-culture/vitamin-b12?srsltid=AfmBOorYbUrvJCWhuCF24v4g-Xs5cCMERVH927fEEAsGkXV5MioxeOot Printed on May 17, 2025.*
Li, H., et al., "The Hypertension Inhibitory Activity of Peptides from Donkey Serum Albumin," Journal of Chinese Institute of Food Science and Technology, 9(6):27-33 (2009), with English abstract.
Vijayasankaran, N., et al., "Effect of Cell Culture Medium Components on Color of Formulated Monoclonal Antibody Drug Substance," Biotechnol Prog., 29(5):1270-1277 (2013).
Extended European Search Report in European Patent Application No. 21747230.7 dated May 22, 2023.
Derfus, G. E., et al., "Red colored IgG4 caused by vitamin $B_{12}$ from cell culture media combined with disulfide reduction at harvest," mAbs, 6(3):679-688 (2014).
Du, C., et al., "Vitamin $B_{12}$ association with mAbs: Mechanism and potential mitigation strategies," Biotechnol Bioeng., 115:900-909 (2018).
International Search Report dated Apr. 13, 2021 in International Application No. PCT/JP2021/003215.
Prentice, K. M., et al., "Hydroxocobalamin association during cell culture results in pink therapeutic proteins," mAbs, 5(6):974-981 (2013).
Vijayasankaran, N. and Varma, S., "Effect of Cell Culture Medium Components on Color of Formulated Monoclonal Antibody Drug Substance," Biotechnol Prog., 29(5):1270-1277 (2013).
Lo, M., et al., Effector-attenuating Substitutions That Maintain Antibody Stability and Reduce Toxicity in Mine, J Biol Chem., 292(9):3900-3908 (2017).

* cited by examiner

*Primary Examiner* — Nora M Rooney
(74) *Attorney, Agent, or Firm* — Nixon & Vanderhye P.C.

(57) ABSTRACT

Provided is a method for producing a composition containing a polypeptide with suppressed coloring, the method comprising the steps of (a) culturing eukaryotic cells containing a nucleic acid encoding a polypeptide in a cell culture medium free of vitamin B12; and (b) collecting a composition containing the polypeptide from the culture.

17 Claims, 10 Drawing Sheets

Specification includes a Sequence Listing.

METHOD FOR PRODUCING COMPOSITION CONTAINING POLYPEPTIDE WITH SUPPRESSED COLORING

CROSS-REFERENCE TO RELATED APPLICATIONS

This application is a U.S. National Phase of PCT Application No. PCT/JP2021/003215, filed Jul. 29, 2021, which claims the benefit of Japanese Patent Application No. 2020-014739, filed Jan. 31, 2020, each of which is incorporated herein by reference in its entirety.

REFERENCE TO SEQUENCE LISTING SUBMITTED ELECTRONICALLY

The content of the electronically submitted sequence listing (Name: 6663_0216 Sequence_Listing.txt; Size: 4.14 KB; and Date of Creation: Jul. 20, 2022) filed with the application is incorporated herein by reference in its entirety.

TECHNICAL FIELD

The present invention provides a method for producing a composition containing a polypeptide with suppressed coloring.

BACKGROUND ART

A method for producing a polypeptide in vitro using a recombinant cell culture is well known, and widely used for industrial-scale production. When a composition containing a polypeptide, e.g. an antibody, is formulated, and provided as a pharmaceutical preparation, it is required to keep the color of the preparation at an acceptable level, for example, a level that meets a regulatory requirement for product marketing.

In particular, a preparation containing an antibody at a high concentration (e.g. 150 mg/mL or more) becomes more intensely colored as it is concentrated, and therefore it is important to keep the color of the preparation at an acceptable level.

A cause of coloring of a preparation containing an antibody has been reported to be adsorption of vitamin $B_{12}$ (hereinafter "VB12") to the antibody (Non Patent Literatures 1 to 3 and Patent Literature 1). One molecule of cobalt is coordinated to one molecule of VB12. VB12 has a cyanocobalamine body and a hydroxycobalamin body, and it has been reported that the hydroxycobalamin body binds to an antibody, so that the molecule is colored pink or red (Non Patent Literatures 1 to 3).

As a culture method intended to prevent coloring of an antibody, a culture method using a culture medium containing specific amounts of vitamins B2, B6, B9, B12 and cystine has been reported (Patent Literature 2). A method has been reported in which coloring is prevented by prevention of conversion of a cyanocobalamine body in a culture medium into hydroxycobalamin and reduction of a disulfide bond of an antibody (Patent Literature 1).

On the other hand, it has been reported that VB12 is a component essential to a cell culture medium for eukaryotic cells (Non Patent Literature 1) and VB12 is a component essential for culturing mammal cells (Patent Document 1).

CITATION LIST

Patent Literature

Patent Literature 1: WO 2018/208743
Patent Literature 2: Japanese Translation of PCT International Application Publication No. 2015-515281

Non Patent Literature

Non Patent Literature 1: MAbs. 2013 Nov. 1; 5(6): 974-981
Non Patent Literature 2: MAbs. 2014 May 1; 6(3): 679-688
Non Patent Literature 3: Biotechnology and Bioengineering. 2018; 115: 900-909

SUMMARY OF INVENTION

Technical Problem

An object of the present invention is to provide a method for solving the coloring problem while maintaining the amount produced and the physical properties of polypeptides within acceptable ranges by modification of a relatively simple production method for polypeptides having a property that easily causes coloring.

Solution to Problem

The present inventors have extensively conducted studies for achieving the above-described object, and resultantly found that use of a culture medium free of VB12 enables suppression of coloring while maintaining the amount of polypeptides produced.

Accordingly, the present invention can be described as the following (1) to (17).

- (1) A method for producing a composition containing a polypeptide with suppressed coloring, the method comprising the steps of
  - (a) culturing eukaryotic cells containing a nucleic acid encoding a polypeptide in a cell culture medium free of vitamin B12; and
  - (b) collecting a composition containing the polypeptide from the culture.
- (2) The method for producing a composition according to (1), wherein the molar concentration ratio of vitamin B12 to the polypeptide is less than 0.26%.
- (3) The method for producing a composition according to (1) or (2), wherein fed-batch culture is performed with an initial culture medium free of vitamin B12 and a feed culture medium free of vitamin B12.
- (4) The method for producing a composition according to (3), wherein the VCD (viable cell density) in the cell culture medium on the seventh day after the start of the fed-batch culture is $80 \times 10^5$ cells/mL or more.
- (5) The method for producing a composition according to any one of (1) to (4), wherein the eukaryotic cells are CHO cells.
- (6) The method for producing a composition according to any one of (1) to (5), wherein the polypeptide is a Fc-containing polypeptide.
- (7) The method for producing a composition according to (6), wherein the Fc-containing polypeptide is an antibody.
- (8) The method for producing a composition according to (6) or (7), wherein the polypeptide contains a modification of at least one amino acid residue selected from amino acid residues at positions 214, 234, 238, 250, 264, 307, 311, 330, 343, 428, 434, 436, 438 and 440 according to EU numbering in the Fc region.

(9) The method for producing a composition according to any one of (6) to (8), wherein the polypeptide contains a modification of at least one selected from 214R, 234Y, 238D, 250V, 264I, 307P, 311R, 330K, 343R, 428L, 434A, 436T, 438R and 440E according to EU numbering in the Fc region.

(10) The method for producing a composition according to any one of (6) to (9), wherein the polypeptide is an antibody comprising a heavy chain constant region containing an amino acid sequence of SEQ ID NO: 1 and a light chain constant region containing an amino acid sequence of SEQ ID NO: 2.

(11) The method for producing a composition according to (10), wherein the antibody is a humanized IgG1 antibody which binds to latent myostatin.

(12) A method for producing a composition containing an antibody with suppressed coloring, the method comprising the steps of:

a) identifying an antibody of interest as an antibody containing a modification of at least one amino acid residue selected from amino acid residues at positions 214, 234, 238, 250, 264, 307, 311, 330, 343, 428, 434, 436, 438 and 440 according to EU numbering in the Fc region;

b) selecting a cell culture medium free of vitamin B12 for the antibody containing a modification of the amino acid residue;

c) culturing eukaryotic cells containing a nucleic acid encoding the antibody containing a modification of the amino acid residue in the cell culture medium selected in step b); and d) collecting a composition containing the antibody from the culture.

(13) The method for producing a composition according to (12), wherein step b) is the step of selecting an initial culture medium free of vitamin B12 and a feed culture medium free of vitamin B12.

(14) The method for producing a composition according to (12) or (13), wherein the eukaryotic cells are CHO cells.

(15) A method for producing an antibody-containing preparation, the method comprising the steps of culturing eukaryotic cells containing a nucleic acid encoding an antibody in a cell culture medium free of vitamin B12; (b) collecting a composition containing the antibody from the culture; and (c) formulating the resulting composition into a pharmaceutical preparation.

(16) A method for suppressing coloring of an antibody in production of an antibody using a recombinant cell culture, the method comprising the steps of (a) culturing eukaryotic cells containing a nucleic acid encoding an antibody in a cell culture medium free of vitamin B12; and (b) collecting a composition containing the antibody from the culture.

(17) The method for producing a composition according to (7), the method for producing an antibody-containing preparation according to (15), or the method for suppressing coloring of an antibody according to (16), wherein the antibody is an anti-IL-8 antibody or an anti-myostatin antibody.

Advantageous Effects of Invention

According to the present invention, a method for producing a composition containing a polypeptide with suppressed coloring is provided.

5 ratus Vi-CELL system (manufactured by Beckman Courter Inc., Model: Vi-CELL XR) in culture of cells that produce antibody B, where VB+ is a culture medium having VB12 contained in an initial culture medium and a feed culture medium, and VB− is a culture medium having no VB12 contained in an initial culture medium and having VB12 contained in a feed culture medium.

Figure 8:
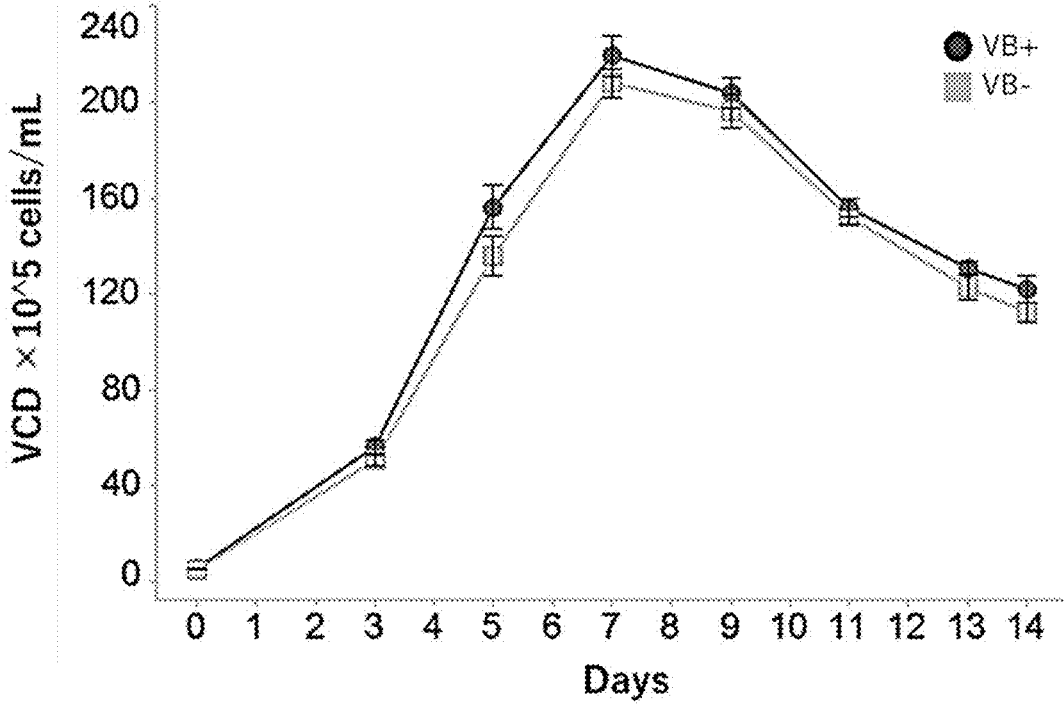

FIG. 8 shows the number of living cells measured on each of 14 culture days using a cell automatic measuring apparatus Vi-CELL system (manufactured by Beckman Courter Inc., Model: Vi-CELL XR) in culture of cells that produce antibody C, where VB+ is a culture medium having VB12 contained in an initial culture medium and a feed culture medium, and VB− is a culture medium having no VB12 contained in an initial culture medium and having VB12 contained in a feed culture medium.

Figure 9:
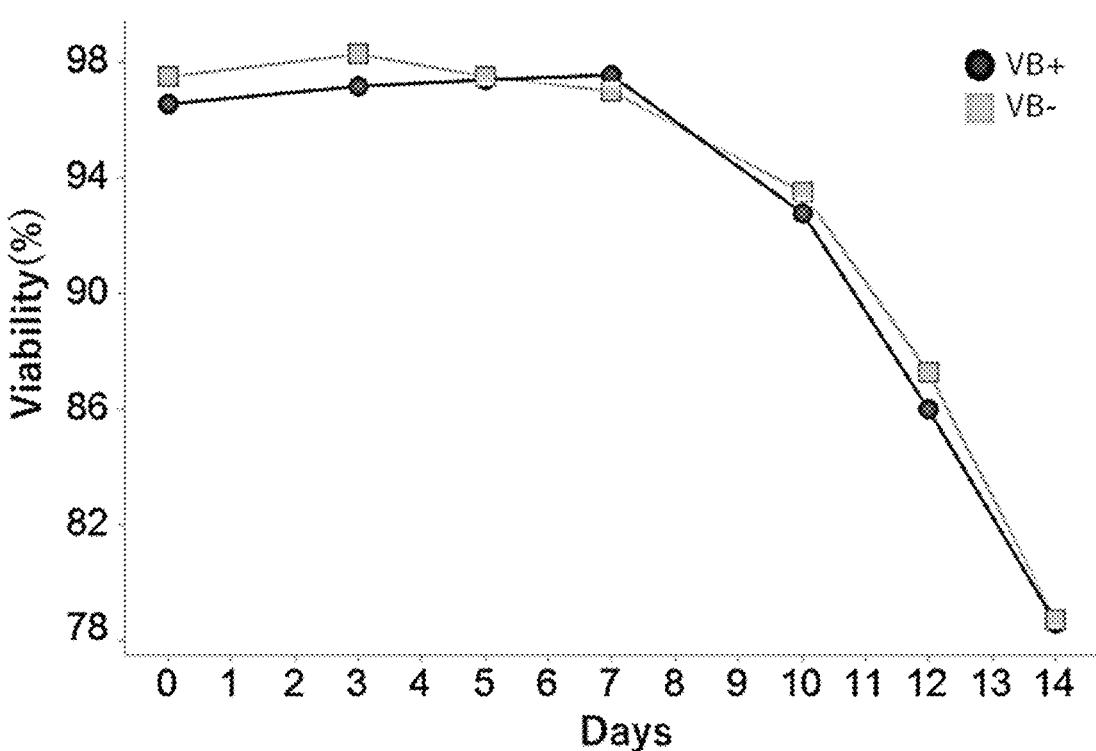

FIG. 9 shows a cell viability measured on each of 14 culture days using a cell automatic measuring apparatus Vi-CELL system (manufactured by Beckman Courter Inc., Model: Vi-CELL XR) in culture of cells that produce antibody B, where VB+ is a culture medium having VB12 contained in an initial culture medium and a feed culture medium, and VB− is a culture medium having no VB12 contained in an initial culture medium and a feed culture medium.

Figure 10:
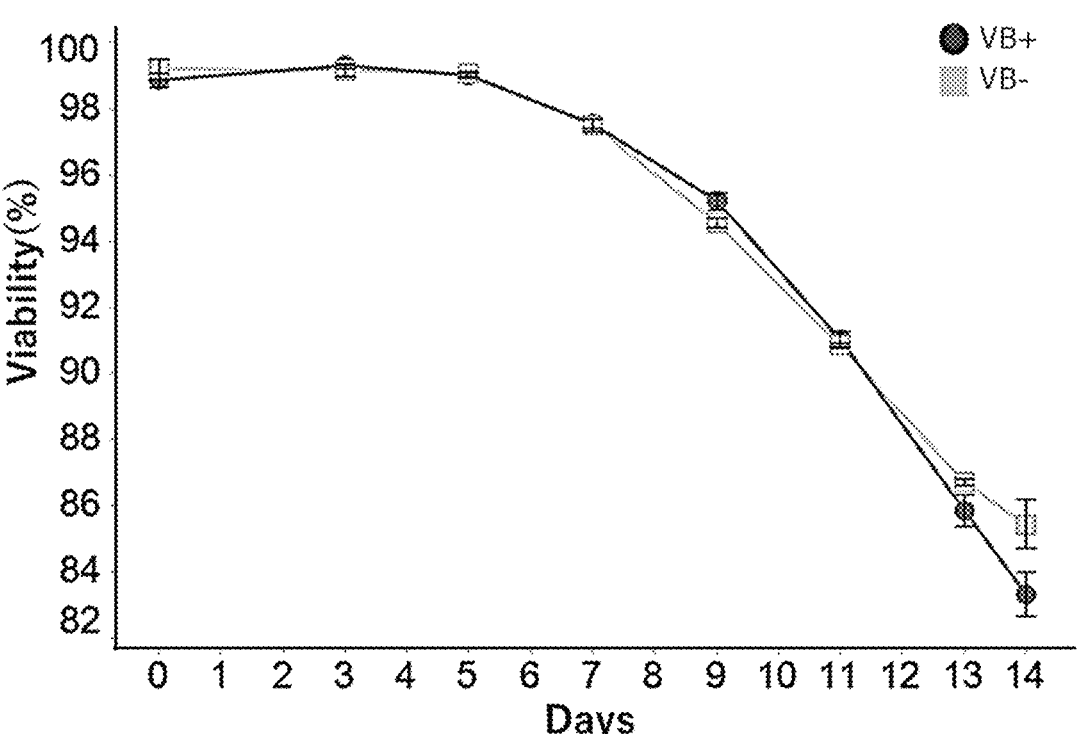

FIG. 10 shows a cell viability measured on each of 14 culture days using a cell automatic measuring apparatus Vi-CELL system (manufactured by Beckman Courter Inc., Model: Vi-CELL XR) in culture of cells that produce antibody C, where VB+ is a culture medium having VB12 contained in an initial culture medium and a feed culture medium, and VB− is a culture medium having no VB12 contained in an initial culture medium and a feed culture medium.

Figure 11:
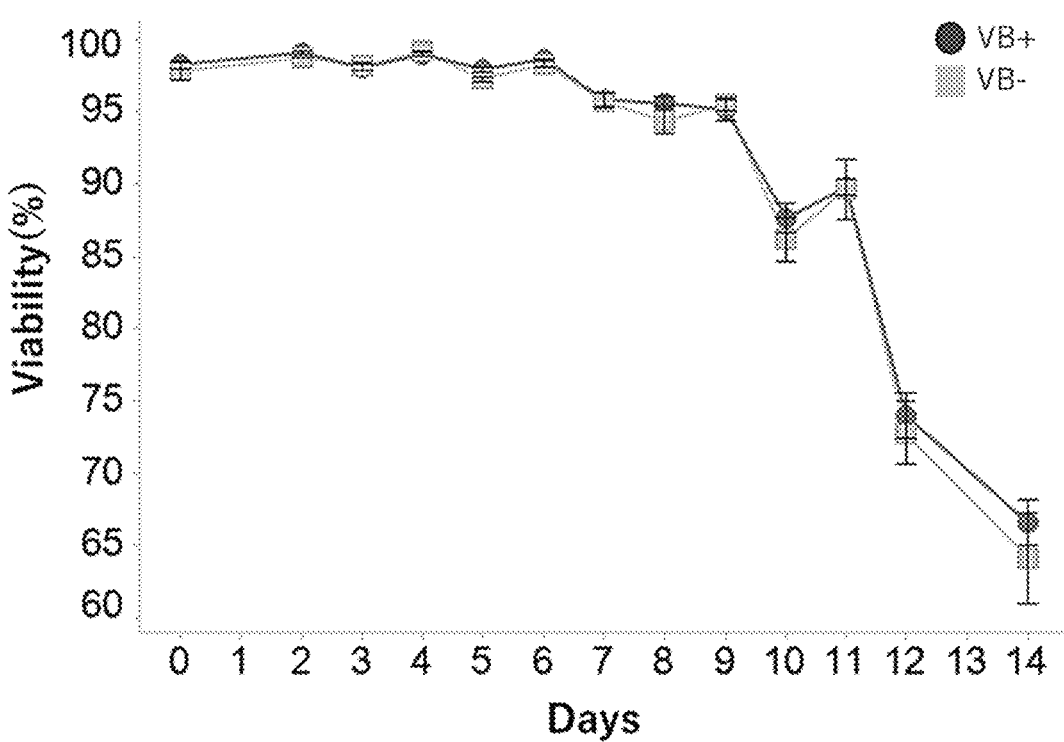

FIG. 11 shows a cell viability measured on each of 14 culture days using a cell automatic measuring apparatus Vi-CELL system (manufactured by Beckman Courter Inc., Model: Vi-CELL XR) in culture of cells that produce antibody B, where VB+ is a culture medium having VB12 contained in an initial culture medium and a feed culture medium, and VB− is a culture medium having no VB12 contained in an initial culture medium and having VB12 contained in a feed culture medium.

Figure 12:
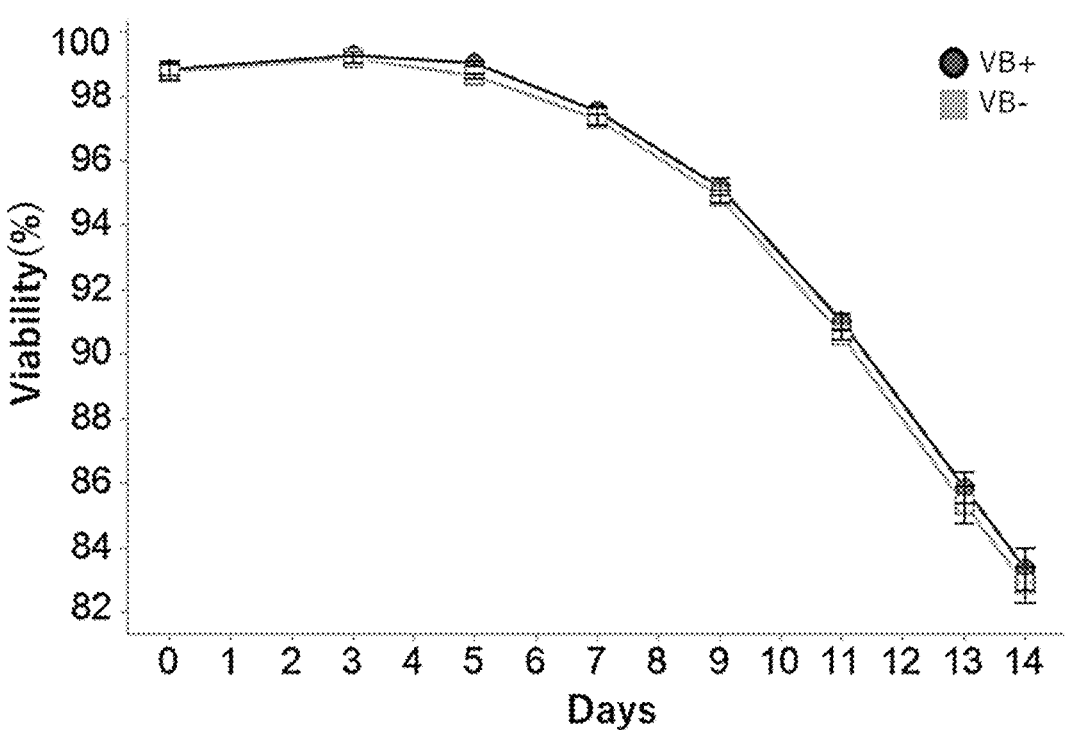

FIG. 12 shows a cell viability measured on each of 14 culture days using a cell automatic measuring apparatus Vi-CELL system (manufactured by Beckman Courter Inc., Model: Vi-CELL XR) in culture of cells that produce antibody C, where VB+ is a culture medium having VB12 contained in an initial culture medium and a feed culture medium, and VB− is a culture medium having no VB12 contained in an initial culture medium and having VB12 contained in a feed culture medium.

Figure 13:
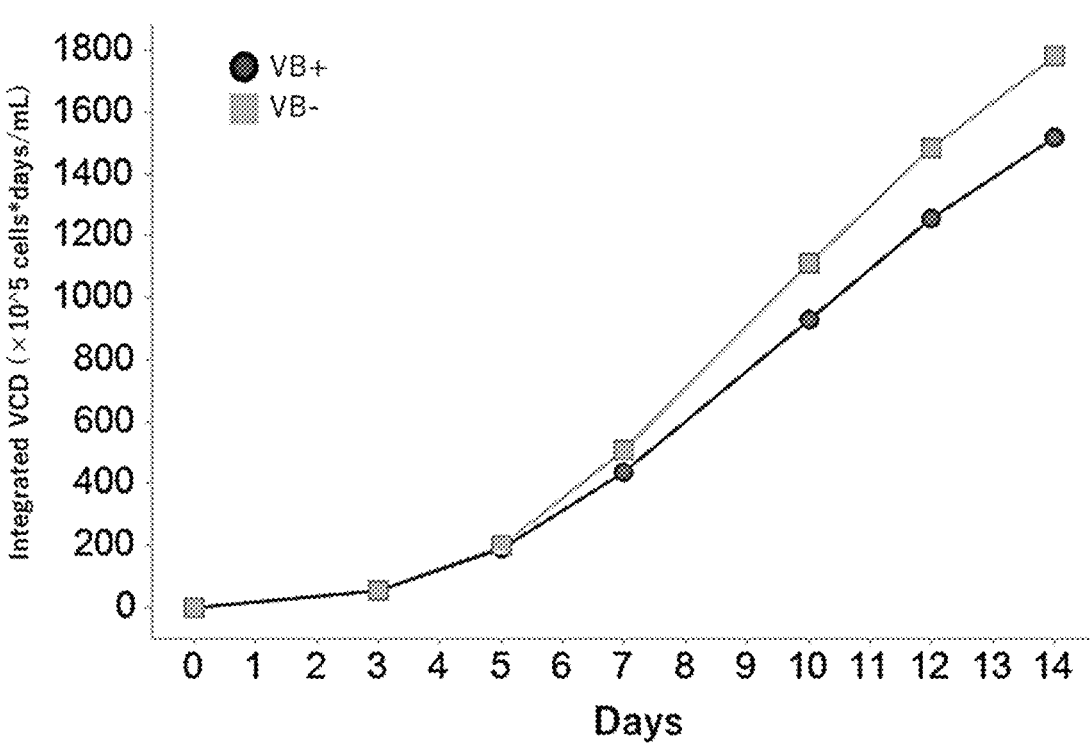

FIG. 13 shows the cumulative number of cells calculated from the number of living cells measured on each of 14 culture days using a cell automatic measuring apparatus Vi-CELL system (manufactured by Beckman Courter Inc., Model: Vi-CELL XR) in culture of cells that produce antibody B, where VB+ is a culture medium having VB12 contained in an initial culture medium and a feed culture medium, and VB− is a culture medium having no VB12 contained in an initial culture medium and a feed culture medium.

Figure 14:
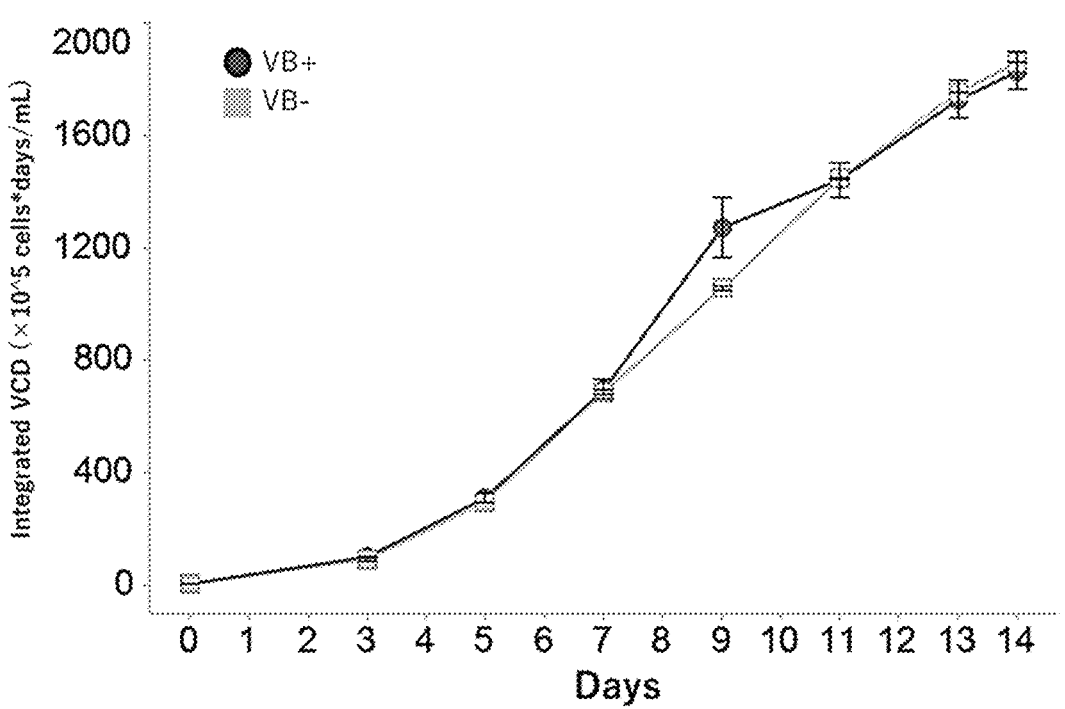

FIG. 14 shows the cumulative number of cells calculated from the number of living cells measured on each of 14 culture days using a cell automatic measuring apparatus Vi-CELL system (manufactured by Beckman Courter Inc., Model: Vi-CELL XR) in culture of cells that produce antibody C, where VB+ is a culture medium having VB12 contained in an initial culture medium and a feed culture medium, and VB− is a culture medium having no VB12 contained in an initial culture medium and a feed culture medium.

Figure 15:
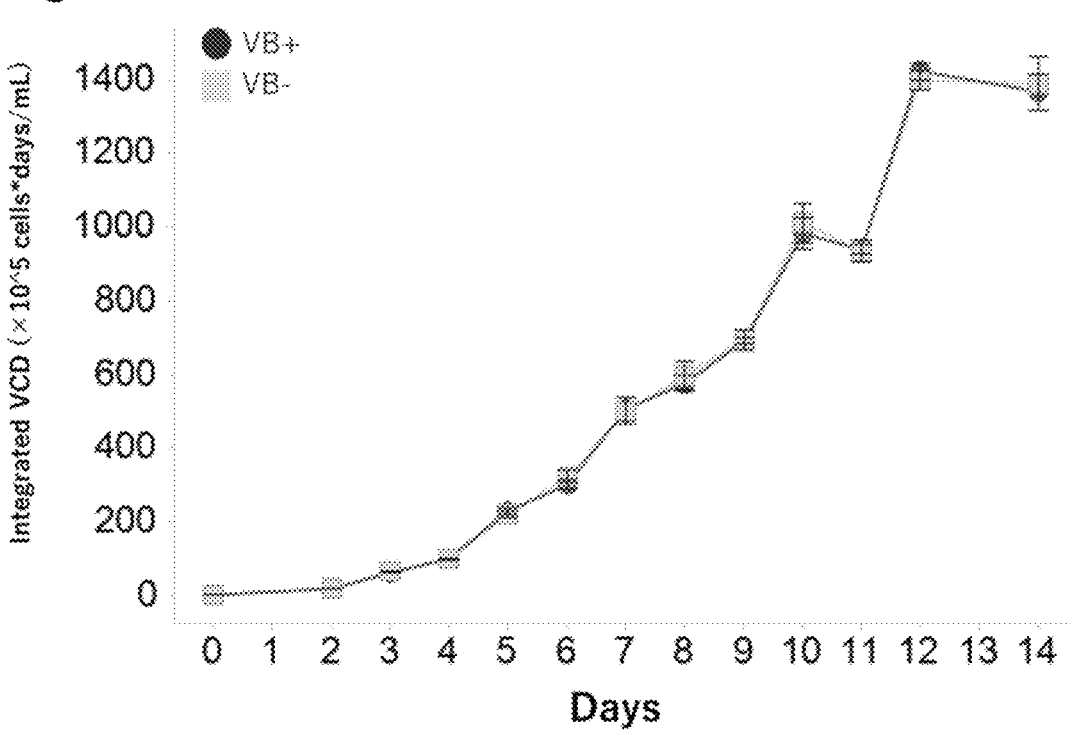

FIG. 15 shows the cumulative number of cells calculated from the number of living cells measured on each of 14 culture days using a cell automatic measuring apparatus Vi-CELL system (manufactured by Beckman Courter Inc., Model: Vi-CELL XR) in culture of cells that produce antibody B, where VB+ is a culture medium having VB12 contained in an initial culture medium and a feed culture medium, and VB− is a culture medium having no VB12 contained in an initial culture medium and having VB12 contained in a feed culture medium.

Figure 16:
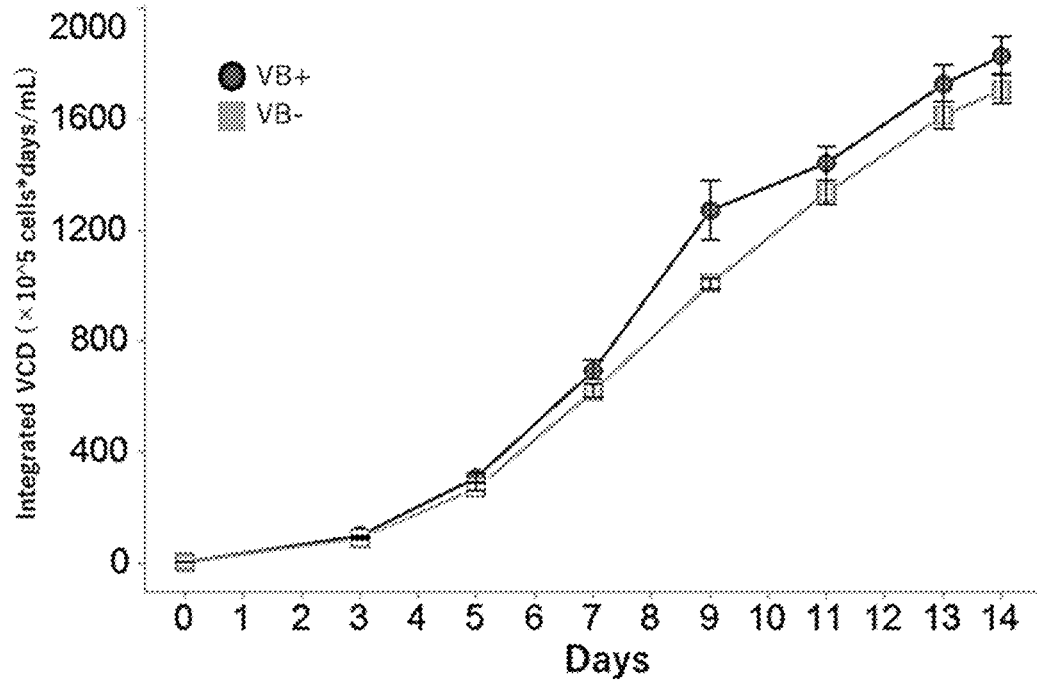

FIG. 16 shows the cumulative number of cells calculated from the number of living cells measured on each of 14 culture days using a cell automatic measuring apparatus Vi-CELL system (manufactured by Beckman Courter Inc., Model: Vi-CELL XR) in culture of cells that produce antibody C, where VB+ is a culture medium having VB12 contained in an initial culture medium and a feed culture medium, and VB− is a culture medium having no VB12 contained in an initial culture medium and having VB12 contained in a feed culture medium.

Figure 17:
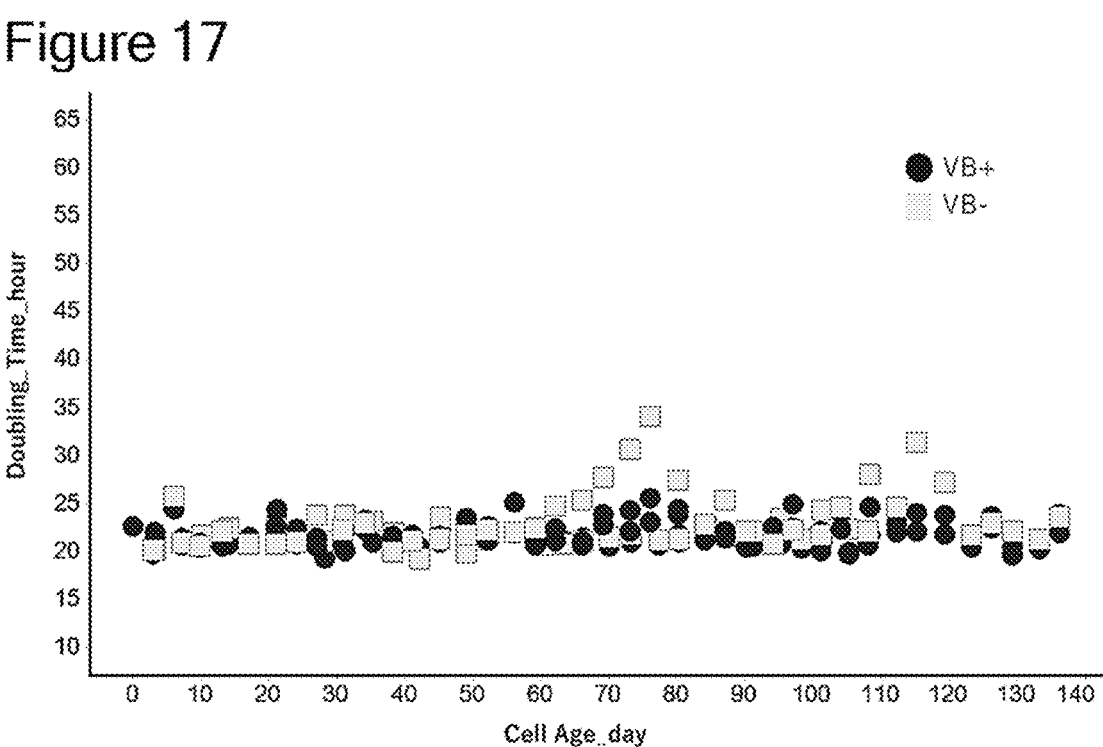

FIG. 17 shows the result of performing passage culture for up to 136 days (39 passages) on a three-day or four-day cycle and plotting a cell growth behavior on each day with the cell doubling time as an indicator, in culture of cells that produce antibody B, where VB+ is a culture medium containing VB12, and VB− is a culture medium free of VB12 (the measurement is performed with a cell automatic measuring apparatus Vi-CELL system (manufactured by Beckman Courter Inc.) and the cell doubling time is calculated).

Figure 18:
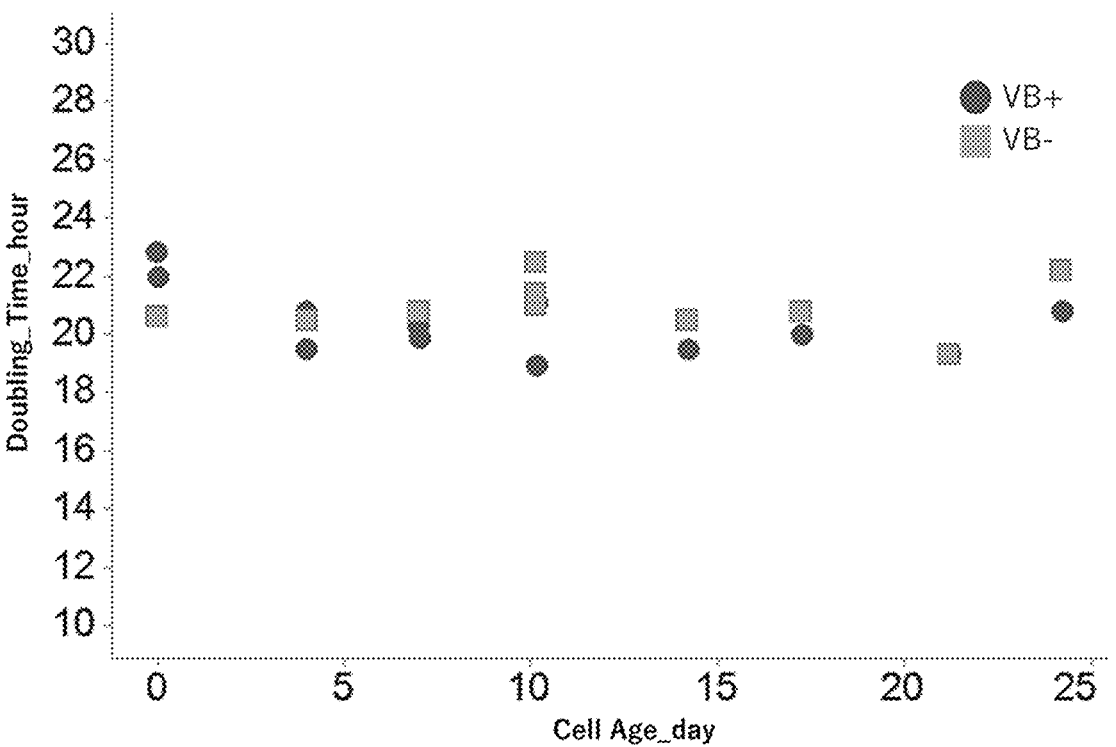

FIG. 18 shows the result of performing passage culture for up to 24 days (7 passages) on a three-day or four-day cycle and plotting a cell growth behavior on each day with the cell doubling time as an indicator, in culture of cells that produce antibody C, where VB+ is a culture medium containing VB12, and VB− is a culture medium free of VB12 (the measurement is performed with a cell automatic measuring apparatus Vi-CELL system (manufactured by Beckman Courter Inc.) and the cell doubling time is calculated).

Figure 19:
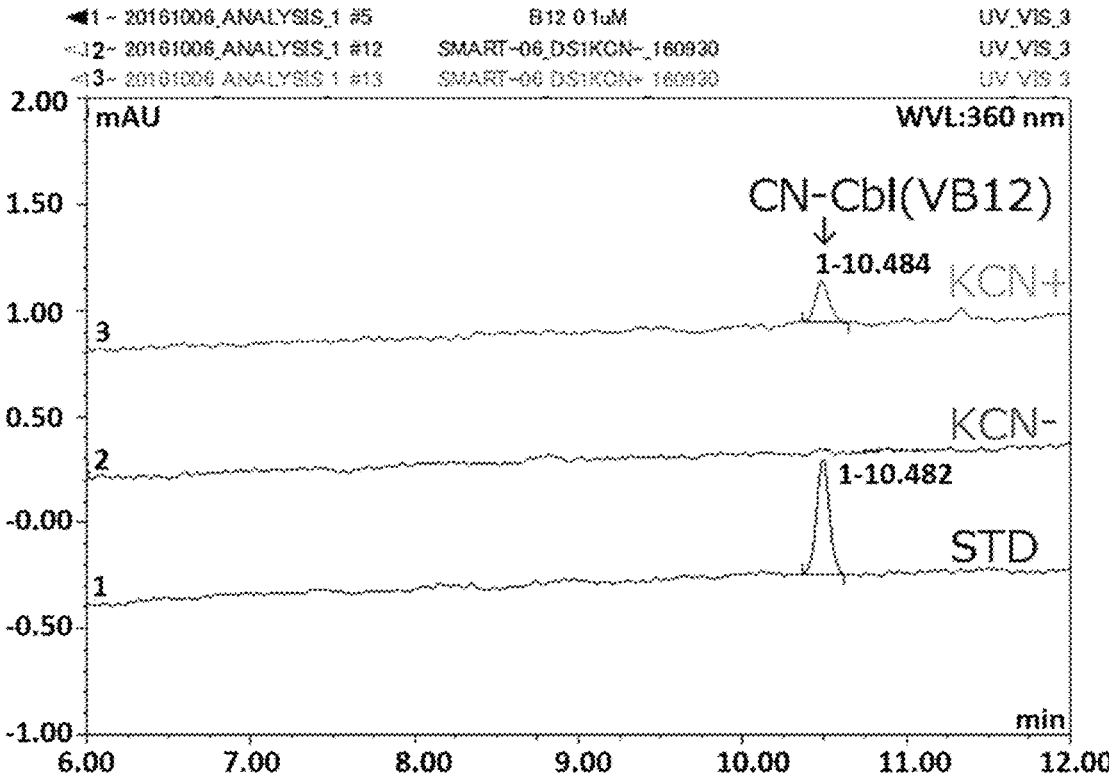

FIG. 19 shows the result of removing an antibody with a 5 KD cutoff filter and analyzing the collected sample by reversed phase chromatography (Column:Acclaim™Polar Advantage II LC) for each of an antibody-containing composition treated with potassium cyanide and an antibody-containing composition which is not treated with potassium cyanide. KCN− represents a potassium cyanide-non-treated sample, KCN+ represents a potassium cyanide-treated sample, and STD represents a peak for VB12.

DESCRIPTION OF EMBODIMENTS

Hereinafter, embodiments of the present invention will be described in detail.

The present invention relates to a method for producing a composition containing a polypeptide with suppressed coloring.

VB12

VB12 refers to cyanocobalamin in the narrow sense, and refers to cobalamin as an inclusive term of vitamin B12 in the broad sense. VB12 as a culture medium component is cyanocobalamin, and when the culture medium component is in the form of an aqueous solution, cyanocobalamin, hydroxycobalamin, aquacobalamin, adenosylcobalamin and methylcobalamin are held in an equilibrium state.

One molecule of cobalt is bound per molecule of VB12. Thus, in Examples of the present application, the relative concentration of VB12 against an antibody was determined by determining the relative concentration of cobalt molecules against the antibody. In the present invention, an initial culture medium and a feed culture medium which are free of VB12 can be used for culturing eukaryotic cells. The culture medium "free of VB12" in the present invention includes not only culture media containing VB12 at a concentration of 0 mg/L but also culture media containing VB12 in an amount that is below a substantial content as a culture medium additive. Specifically, the term "free of VB12" applies to a case where the concentration of cobalt molecules contained in VB12 is less than 20 ppb as a limit for quantitative determination when culture is performed under the same conditions as in Example 1 of the present invention using the culture medium and the resulting antibody-containing composition (antibody concentration: about 30 mg/mL) is measured by ICP-MS.

Eukaryotic Cell

The eukaryotic cell is a cell having nucleus covered with a nuclear membrane. The "eukaryotic cell containing a nucleic acid encoding a polypeptide" in the present invention is a host cell which can be used as a production system for producing a desired polypeptide. The cell may be a natural cell capable of producing a desired polypeptide, or a cell in which a nucleic acid encoding (or expressing) a desired polypeptide is artificially introduced, and a transformed cell is preferable in which a nucleic acid encoding a desired polypeptide is introduced. An example of the transformed cell is a polypeptide producing strain obtained by introducing exogenous DNA encoding a desired polypeptide into a eukaryotic cell using a gene-recombination technique. Therefore, the phrase "containing a nucleic acid encoding a polypeptide" can be replaced with "a nucleic acid encoding a polypeptide is artificially introduced" or "an exogenous nucleic acid encoding a polypeptide is introduced".

A typical example of the eukaryotic cell in the present invention is a cell suitable as a host for production of a recombinant protein, which can be selected from cells derived from insects, fish, amphibia, reptiles or mammals. A preferred example of the eukaryotic cell in the present invention is a mammal cell. The mammal cell is selected from a CHO cell, a NSO cell, a Sp2/0 cell, a COS cell, a HEK cell, a BHK cell, a PER.C6 (R) cell, a hybridoma cell and the like, and is more preferably a CHO cell.

Cell Culture Medium

In the present invention, the cell culture medium is a culture medium used for culturing cells containing a nucleic acid encoding a polypeptide, and can also be referred to simply as a culture medium. As the cell culture medium, a commercially available culture medium or a known culture medium can be appropriately used. Except for the culture medium free of VB12 which is used in the present invention, a normal culture media contains VB12 as an essential component necessary for transcriptional activity and nucleic acid synthesis in cells. In Examples of the present invention, a culture medium was used in which while the composition of an existing culture medium is maintained, only the VB12 component is excluded, removed or reduced in amount.

The type of culture medium suitable for a specific cell strain can be appropriately selected by a person skilled in the art. For example, culture media such as IMDM (Iscove's Modified Dulbecco's Medium), DMEM (Dulbecco's Modified Eagle Medium), Ham's F12 Medium, D-MEM/F-12 1:1

Mixture (Dulbecco's Modified Eagle Medium: Nutrient Mixture F-12), RPMI1640, CHO-S-SFM II (Invitrogen Company), CHO-SF (Sigma-Aldrich Co. LLC), EX-CELL 301 (JRH biosciences Inc.), CD-CHO (Invitrogen Company), IS CHO-V (Irvine Scientific, Inc.) and PF-ACF-CHO (Sigma-Aldrich Co. LLC) can be used as well known culture media or commercially available culture media for culturing animal cells, and of course, a person skilled in the art understands that there is no limitation on these culture media. Many culture media optimized for cell growth and improvement of the yield in production of antibodies and recombinant proteins are well known to a person skilled in the art.

Examples of the culture medium which can be used for culturing CHO cell strains producing a humanized antibody (IgG1 antibody) that binds to latent myostatin used in Examples include IMDM, DMEM, Ham's F12 Medium, and combinations thereof.

Cell Culture

In general, cell culture methods are classified into batch culture, continuous culture and fed-batch culture.

The batch culture is a culture method in which a small amount of a seed culture solution is added to a culture medium, and cells are grown without adding a fresh culture medium into the culture medium or discharging the culture solution.

The continuous culture is a culture method in which a culture medium is continuously added and continuously discharged during culture. The continuous culture includes perfusion culture.

The fed-batch culture is also called semi-batch culture because it is in the middle between batch culture and continuous culture. In the culture method, a culture medium is continuously or sequentially added during culture, but continuous discharge of a culture solution as in continuous culture is not performed. The culture medium added during fed-batch culture (hereinafter, referred to as a feed culture medium) is not required to be a culture medium identical to a culture medium that has been already used for culture (hereinafter, referred to as an initial culture medium), and a different culture medium may be added, or only a specific component may be added. Alternatively, the feed culture medium may be a culture medium having the same composition as that of the initial culture medium.

In the present invention, any culture method selected from batch culture, continuous culture and fed-batch culture may be used, and fed-batch culture is preferably used.

For culturing cells to produce a desired polypeptide, normally, a certain amount of a seed culture medium containing the cells is added to an initial culture medium, and the cells are cultured. Further, for increasing the amount of a desired polypeptide produced, a feed culture medium is added during culture.

The seed culture medium is a culture medium in which cells producing a desired polypeptide (working cell bank) are amplified and cultured to obtain a cell number necessary for transferring the cells to a culture medium for ultimately producing a desired polypeptide (initial culture medium). The initial culture medium is normally a culture medium in which cells are cultured to produce a desired polypeptide, where the culture medium is used in the initial stage of the culture of cells. The feed culture medium is normally a culture medium added to a culture medium during initial culture. The feed culture medium may be added in divided parts. The feed culture medium may be continuously or intermittently added.

In the present invention, passage culture of cells is performed in a seed culture medium, a certain amount of the seed culture medium containing the cells is then added to an initial culture medium, and the cells are cultured in the initial culture medium for producing a desired polypeptide. Further, in some cases, a feed culture medium is added to the culture medium one or more times during culture.

The fed-batch culture is further classified according to the way of performing feeding. The constant-rate fed-batch culture is a culture method in which a certain amount of a feed culture medium is continuously added to an initial culture medium.

Polypeptide, Composition Containing Polypeptide, Collection of Composition Containing Polypeptide The polypeptide for use in the present invention is preferably a Fc-containing polypeptide containing a region corresponding to Fc of an antibody, more preferably an antibody.

Composition containing polypeptide (polypeptide-containing composition) means a composition containing a polypeptide and other components. In Examples of the present invention, a composition containing a polypeptide can be collected from a culture obtained by a cell culture step for polypeptide production. The term "collect" mentioned here means that from a culture or culture solution obtained by the cell culture step, a supernatant liquid (culture supernatant liquid) containing a polypeptide is collected or a filtrate containing a polypeptide is collected using a filter.

The solution collected in this way can undergo the steps of purification by affinity column chromatography or the like and concentration to prepare a composition containing a polypeptide at an appropriate concentration.

When the polypeptide is a Fc-containing polypeptide or an antibody, the composition containing a polypeptide (polypeptide-containing composition) can be replaced with a composition containing a Fc-containing polypeptide (Fc-containing polypeptide-containing composition) or a composition containing an antibody (antibody-containing composition).

Fc Region (Fc)

The term "Fc region" (or referred to simply as Fc) includes a natural sequence Fc region and a variant Fc region. Although the boundary of the Fc region of an immunoglobulin heavy chain may change, the Fc region is a region composed of a hinge portion or a part thereof and CH2 and CH3 domains in an antibody molecule. The Fc region is not limited as long as it is a Fc region of an antibody (IgA, IgD, IgE, IgG or IgM), particularly IgG, and the Fc region is preferably a Fc region of human IgG (IgG1, IgG2, IgG3 or IgG4), more preferably a Fc region of human IgG1.

Suppression of Coloring

The composition containing a polypeptide with suppressed coloring in the present invention is a composition containing a polypeptide with reduced coloring caused by adsorption of VB12, specifically red or pink coloring. In Examples of the present invention, a polypeptide (antibody)-containing composition with a polypeptide (antibody) concentration adjusted to about 30 mg/mL was evaluated as being colorless in visual assessment, and it was confirmed that coloring was suppressed. In the composition containing a polypeptide (antibody) with suppressed coloring, the molar concentration ratio [%] of VB12 to the polypeptide which is determined under the conditions in Example 1 is less than 0.26, preferably less than 0.2, more preferably less than 0.1, still more preferably less than 0.05.

Identification of Antibody and Selection of Cell Culture Medium

In an embodiment of the present invention, an antibody which is easily colored is identified in advance, and for this antibody, a culture step different from a normal culture step and suitable for suppression of coloring is selected. In this embodiment, there is the step of first identifying an polypeptide of interest as a polypeptide containing a modification in at least one amino acid residue selected from amino acid residues at positions 214, 234, 238, 250, 264, 307, 311, 330, 343, 428, 434, 436, 438 and 440 according to EU numbering in the Fc region. The term "identifying" includes not only identifying a specific modification position in the polypeptide by an analytic method, but also previously recognizing that a polypeptide of interest contains the modification.

Next, for the antibody confirmed as containing a modification of an amino acid residue, a step different from a normal culture step is selected. That is, in the normal culture step, a cell culture medium containing VB12 as an essential component (normal cell culture medium) is used, whereas in the culture step for the antibody, a cell culture medium free of VB12 is used instead of the normal cell culture medium. Here, as the cell culture medium free of VB12, one having the same composition as the composition of the normal cell culture medium except that only VB12 is excluded can be used.

With the cell culture medium selected in this way, a composition containing a polypeptide is produced through the step of culturing cells containing a nucleic acid encoding the polypeptide and the step of collecting a composition containing the polypeptide from the culture.

EXAMPLES

Hereinafter, the present invention will be described specifically by way of Examples. These Examples are intended to illustrate the present invention, and do not limit the scope of the present invention.

In Examples, the following antibodies, cells and culture media were used.

Antibody:

As antibody A, an anti-myostatin antibody was used which is a humanized IgG1 antibody comprising a heavy chain constant region containing an amino acid sequence of SEQ ID NO: 1 and a light chain constant region containing an amino acid sequence of SEQ ID NO: 2, and binds to latent myostatin. This antibody contains modifications of 214R, 234Y, 238D, 250V, 264I, 307P, 311R, 330K, 343R, 428L, 434A, 436T, 438R and 440E according to EU numbering in the Fc region.

As antibody B, an anti-IL-8 antibody was used which is disclosed in WO/2016/125495 or WO/2017/046994 and binds to IL-8.

As antibody C, an anti-FIX(a)/FX dual-specificity antibody was used which is disclosed in WO 2019065795 and binds to both FIX(a) and FX.

Cell:

As CHO cells, a CHO-DXB11-derived strain was used.

Culture Medium:

As initial culture media and feed culture media, culture media manufactured by Thermo Fisher Scientific, Inc. and FUJIFILM Wako Pure Chemical Corporation were used. In Examples, an initial culture medium containing VB12 (initial culture medium having a relative VB12 concentration of 100%), an initial culture medium completely free of VB12 and identical to the above-mentioned initial culture medium in composition except for VB12 (initial culture medium having a relative VB12 concentration of 0%) and an initial culture medium obtained by mixing the above-mentioned two culture media at a ratio of 1:1 (initial culture medium having a relative VB12 concentration of 50%) were provided as initial culture media. A feed culture medium containing VB12 (feed culture medium having a relative VB12 concentration of 100%) and a feed culture medium completely free of VB12 and identical to the above-mentioned feed culture medium in composition except for VB12 (feed culture medium having a relative VB12 concentration of 0%) were provided as feed culture media.

Example 1. Study on Effect of VB12 on Coloring of Antibody

Cells producing antibody A were cultured under the same conditions by constant-rate fed-batch culture using a 1 L to 25 L culture apparatus for each of samples 1 to 9 in which the initial culture medium and the feed culture medium are combined as in Table 1. Culture was performed for 14 days at a pH of 6.7 to 7.2 and at 34° C. to 38° C., and the feed culture medium was added on the third day after the start of the culture.

A composition containing an antibody was collected from the culture solution after culturing for 14 days, and purified by affinity column chromatography with Protein A, and the eluate was then concentrated. Samples 1 to 8 were adjusted to an antibody concentration of about 30 mg/mL (26.7 mg/mL to 31.4 mg/mL). Sample 9 was further concentrated to an antibody concentration of 200 mg/mL or more.

For the thus-obtained antibody-containing combination, coloring and the VB12 content were evaluated. The coloring was evaluated by visual assessment. For samples 1, 5 and 7, the composition was slightly colored (slightly red). For sample 9, the composition was colored (red). On the other hand, for samples 2 to 4 and 6 to 8, the composition was not colored (colorless).

Since one molecule of cobalt is bound per molecule of VB12 in the antibody-containing composition, the concentration of cobalt contained in the antibody-containing composition was measured by ICP-MS (inductively coupled plasma-mass spectrometry), and the molar concentration ratio of cobalt to antibody (cobalt/antibody [%]) was calculated to estimate the content of VB12 (molar concentration ratio of VB12 to antibody (VB12/antibody [%])). Table 1 shows the results.

The experiment results demonstrated that VB12 contained in the antibody-containing composition was a cause of coloring. In addition, it was confirmed that suppression of VB12 contained in the initial culture medium and the feed culture medium enabled suppression of VB12 contained in the antibody-containing composition after culture.

Example 2. Study on Effect of VB12 in Culture Medium on Cell Culture

Figure 1:
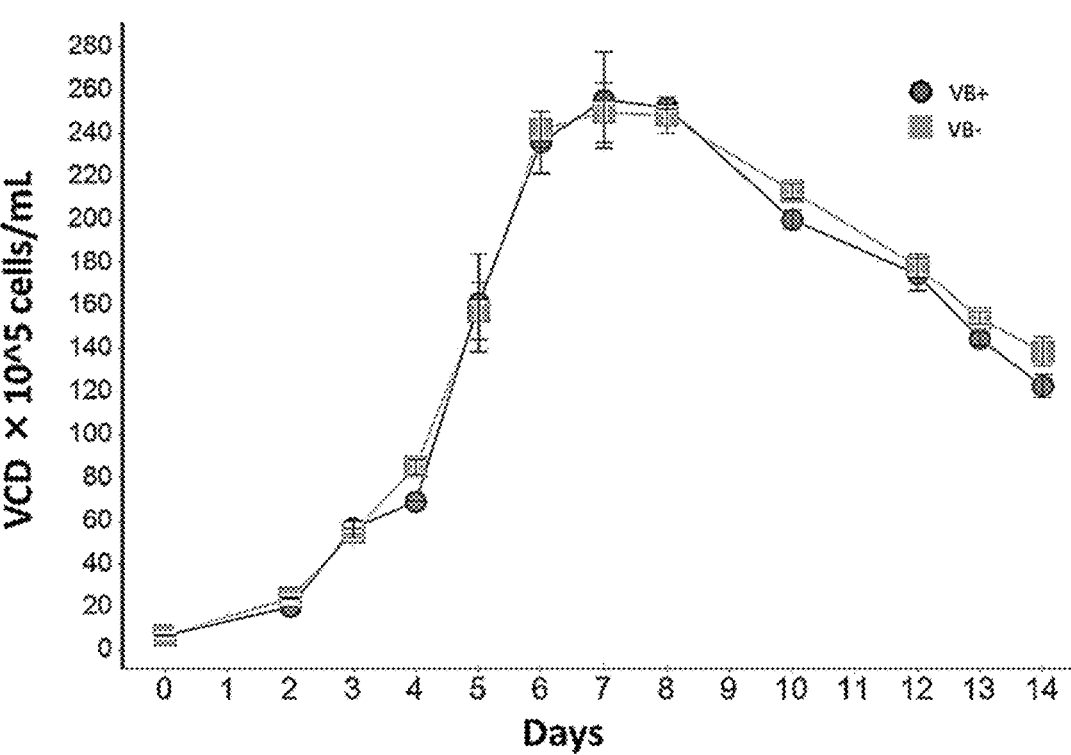
FIG. 1 shows the number of living cells measured on each of 14 culture days using a cell automatic measuring apparatus Vi-CELL system (manufactured by Beckman Courter Inc., Model: Vi-CELL XR) in culture of cells that produce a polypeptide (antibody A: anti-myostatin antibody), where VB+ is a culture medium having VB12 contained in an initial culture medium and a feed culture medium, and VB− is a culture medium having no VB12 contained in an initial culture medium and a feed culture medium.
Figure 2:
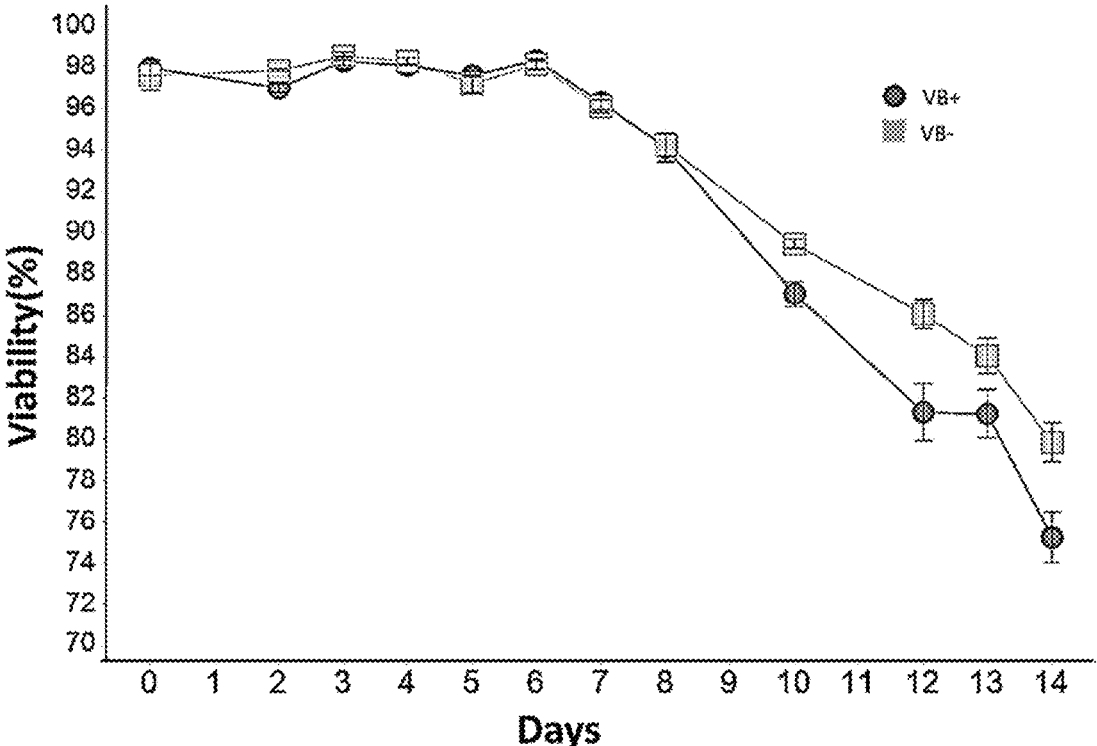
FIG. 2 shows a cell viability measured on each of 14 culture days using a cell automatic measuring apparatus Vi-CELL system (manufactured by Beckman Courter Inc., Model: Vi-CELL XR) in culture of cells that produce antibody A, where VB+ is a culture medium having VB12 contained in an initial culture medium and a feed culture medium, and VB− is a culture medium having no VB12 contained in an initial culture medium and a feed culture medium.
Figure 3:
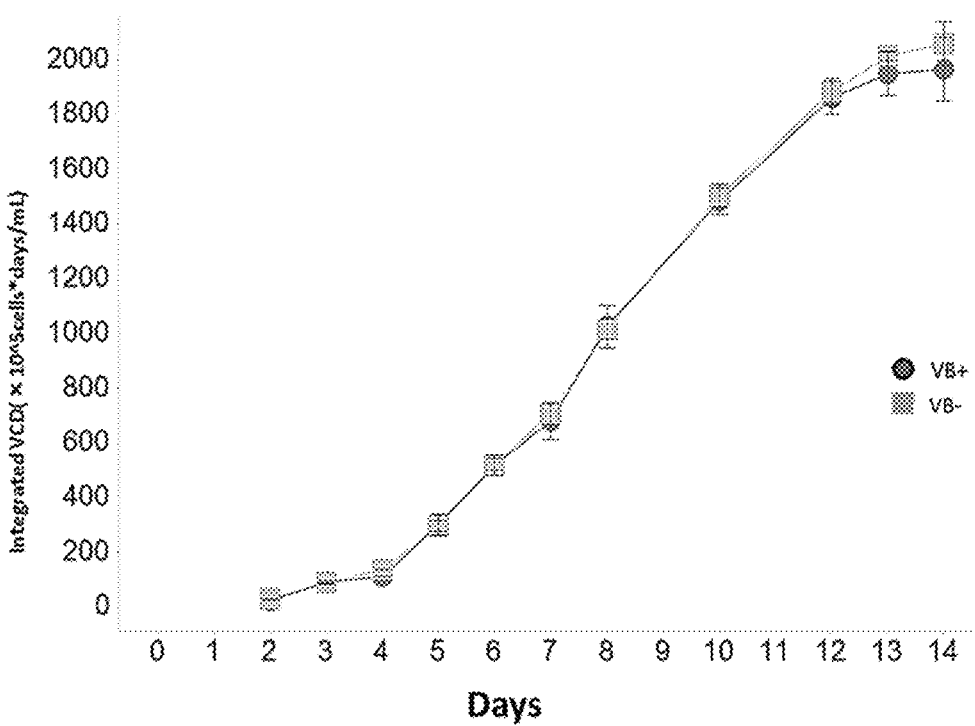
FIG. 3 shows the cumulative number of cells calculated from the number of living cells measured on each of 14 culture days using a cell automatic measuring apparatus Vi-CELL system (manufactured by Beckman Courter Inc., Model: Vi-CELL XR) in culture of cells that produce antibody A, where VB+ is a culture medium having VB12 contained in an initial culture medium and a feed culture medium, and VB− is a culture medium having no VB12 contained in an initial culture medium and a feed culture medium.

Effects of the presence or absence of VB12 in the culture medium on the number of living cells, the cell viability and the cumulative number of cells were observed through cell culture performed under the same conditions as in Example 1. The results showed that culture with a culture medium having no VB12 contained in an initial culture medium and a feed culture medium (VB−) was substantially comparable in the number of living cells on each day, the cell viability and the cumulative number of cells to culture with a culture medium having VB12 contained in an initial culture medium and a feed culture medium (VB+). (FIGS. 1, 2 and 3)

Cells producing antibody B or cells producing antibody C were cultured under the same conditions by constant-rate fed-batch culture using a 1 L culture apparatus for each of sample 10 (VB+) and sample 11 (VB−) in which the condition of an initial culture medium and a feed culture medium is set as in Table 1-1. Culture was performed for 14 days at a pH of 6.7 to 7.2 and at 34° C. to 38° C., and the feed culture medium was added on the third day after the start of the culture.

Effects of the presence or absence of VB12 in the culture medium on the number of living cells, the cell viability and the cumulative number of cells were observed in cell culture under these conditions. The results showed that culture with a culture medium having no VB12 contained in an initial culture medium and a feed culture medium (VB−) was substantially comparable in the number of living cells on each day, the cell viability and the cumulative number of cells to culture with a culture medium having VB12 contained in an initial culture medium and a feed culture medium (VB+) (FIGS. 5, 6, 9, 10, 13 and 14).

Cells producing antibody B or cells producing antibody C were cultured under the same conditions by constant-rate fed-batch culture using a 1 L culture apparatus for each of sample 10 (VB+) and sample 12 (VB−) in which condition of an initial culture medium and a feed culture medium is set as in Table 1-1. Culture was performed for 14

TABLE 1

| | | Sample No. | | | | | | | | |
|---|---|---|---|---|---|---|---|---|---|---|
| | | 1 | 2 | 3 | 4 | 5 | 6 | 7 | 8 | 9 |
| Relative VB12 concentration (%) | Initial culture medium | 100% | 0% | 100% | 50% | 100% | 0% | 100% | 50% | 100% |
| | Feed culture medium | 100% | 0% | 0% | 0% | 100% | 0% | 0% | 0% | 100% |
| Visual assessment on coloring | | Slightly red | Colorless | Colorless | Colorless | Slightly red | Colorless | Slightly red | Colorless | Red |
| Concentration of antibody in composition after purification/concentration [mg/mL] | | 31.4 | 30.3 | 28.1 | 26.7 | 30.1 | 30.9 | 31.4 | 31.3 | 237 |
| Concentration of cobalt [ppb] | | 41 | <20 | <20 | <20 | 38 | <20 | 20 | <20 | 247 |
| Cobalt/antibody [%] | | 0.33 | — | — | — | 0.7 | — | 0.3 | — | 0.26 |
| VB12/ANTIBODY [%] | | 0.33 | — | — | — | 0.7 | — | 0.3 | — | 0.26 |

* The concentration of cobalt [ppb], cobalt/antibody [%] and VB12/antibody [%] of samples 2 to 4, 6, and 8 are below the limit for quantitative determination.

days at a pH of 6.7 to 7.2 and at 34° C. to 38° C., and the feed culture medium was added on the third day after the start of the culture.

Effects of the presence or absence of VB12 in the culture medium on the number of living cells, the cell viability and the cumulative number of cells were observed in cell culture under these conditions. The results showed that culture with a culture medium having no VB12 contained in an initial culture medium and having VB12 contained in a feed culture medium (VB−) was substantially comparable in the number of living cells on each day, the cell viability and the cumulative number of cells to culture with a culture medium having VB12 contained in an initial culture medium and a feed culture medium (VB+) (FIGS. 7, 8, 11, 12, 15 and 16).

TABLE 1-1

| | Sample No. | 10 | 11 | 12 |
|---|---|---|---|---|
| Relative VB12 concentration (%) | Initial culture medium | 100% | 0% | 0% |
| | Feed culture medium | 100% | 0% | 100% |

Example 3. Study on Effect of VB12 in Culture Medium on Amount of Antibody Produced Effects of the presence or absence of VB12 in the culture medium on the amount of the antibody produced were observed through cell culture performed under the same conditions as in Example 1. The results showed that culture with a culture medium having no VB12 contained in an initial culture medium and a feed culture medium (VB−) was substantially comparable in the amount of the antibody produced after culture for 14 days to culture with a culture medium having VB12 contained in an initial culture medium and a feed culture medium (VB+) (Table 2: the production amount of the antibody in control culture using VB+ is defined as 100%).

Cells producing antibody B were also cultured under the conditions in Table 1-1, and effects of the presence or absence of VB12 in the culture medium on the production amount of the antibody were observed. The results showed that culture with a culture medium having no VB12 contained in an initial culture medium and a feed culture medium (VB−) as the condition for sample 11 and culture with a culture medium having no VB12 contained in an initial culture medium and having VB12 contained in a feed culture medium (VB−) as the condition for sample 12 were substantially comparable in the production amount of the antibody after culture for 14 days to culture with a culture medium having VB12 contained in an initial culture medium and a feed culture medium (VB+) as the condition for sample 10 (Tables 2-1 and 2-2: the production amount of the antibody in control culture using VB+ is defined as 100%).

TABLE 2

| | Amount produced (%) | Standard error (%) |
|---|---|---|
| VB+ | 100 | 1.36 |
| VB− | 104.6 | 1.53 |

TABLE 2-1

Antibody B
VB+ corresponds to the condition for sample No 10 and
VB− corresponds to the condition for sample No 11

| | Amount produced (%) |
|---|---|
| VB+ | 100 |
| VB− | 100.5 |

TABLE 2-2

Antibody B
VB+ corresponds to the condition for sample No 10 and
VB− corresponds to the condition for sample No 12

| | Amount produced (%) | Standard error (%) |
|---|---|---|
| VB+ | 100 | 1.709 |
| VB− | 100.7 | 1.861 |

Cells producing antibody C were also cultured under the conditions in Table 1-1, and effects of the presence or absence of VB12 in the culture medium on the production amount of the antibody were observed. The results showed that culture with a culture medium having no VB12 contained in an initial culture medium and a feed culture medium (VB−) as the condition for sample 11 and culture with a culture medium having no VB12 contained in an initial culture medium and having VB12 contained in a feed culture medium (VB−) as the condition for sample 12 were substantially comparable in the production amount of the antibody after culture for 14 days to culture with a culture medium having VB12 contained in an initial culture medium and a feed culture medium (VB+) as the condition for sample 10 (Tables 2-3 and 2-4: the production amount of the antibody in control culture using VB+ is defined as 100%).

TABLE 2-3

Antibody C
VB+ corresponds to the condition for sample No 10 and
VB− corresponds to the condition for sample No 11

| | Amount produced (%) | Standard error (%) |
|---|---|---|
| VB+ | 100 | 1.027 |
| VB− | 106.2 | 1.558 |

TABLE 2-4

Antibody C
VB+ corresponds to the condition for sample No 10 and
VB− corresponds to the condition for sample No 12

| | Amount produced (%) | Standard error (%) |
|---|---|---|
| VB+ | 100 | 1.027 |
| VB− | 107.4 | 1.623 |

Example 4. Study on Effect of VB12 in Culture Medium on Physical Properties of Antibody Cell culture, affinity column chromatography treatment and concentration were performed under the same conditions as in Example 1, and antibodies in the obtained compositions were analyzed to examine effects of the presence or absence of VB12 in the culture medium on the physical properties of the antibody. The results showed that the antibody obtained by culture with a culture medium having no VB12 contained in an initial culture medium and a feed culture medium (VB–) was substantially comparable in glycosylation (afcosyl, fucosyl, galactosyl, high mannose and hybrid), cell-derived protein (HCP), cell-derived DNA (DNA), proportion of charge variants (acidic and basic) and proportion of polymers (HMWs) to the antibody obtained by culture with a culture medium having VB12 contained in an initial culture medium and a feed culture medium (VB+) (Table 3: each physical property of the antibody obtained by control culture using VB+ is defined as 100%).

TABLE 3

| | Afucosyl | Fucosyl | Galactosyl | High mannose | Hybrid | HCP | DNA | Acidic | Basic | HMWs |
|---|---|---|---|---|---|---|---|---|---|---|
| VB+ (%) | 100 | 100 | 100 | 100 | 100 | 100 | 100 | 100 | 100 | 100 |
| VB– (%) | 93.5 | 100.4 | 84.0 | 94.5 | 88.3 | 93.8 | 113.8 | 91.4 | 106.8 | 113.9 |
| VB+ Standard error (%) | 8.2 | 0.3 | 3.1 | 2.3 | 14.6 | 4.9 | 31.4 | 1.6 | 2.5 | 21.8 |
| VB– Standard error (%) | 5.4 | 0.2 | 1.7 | 2.3 | 6.6 | 8.9 | 26.2 | 1.0 | 1.3 | 14.0 |

Example 5. Study on Effect of VB12 in Culture Medium on Cell Passage

Figure 4:
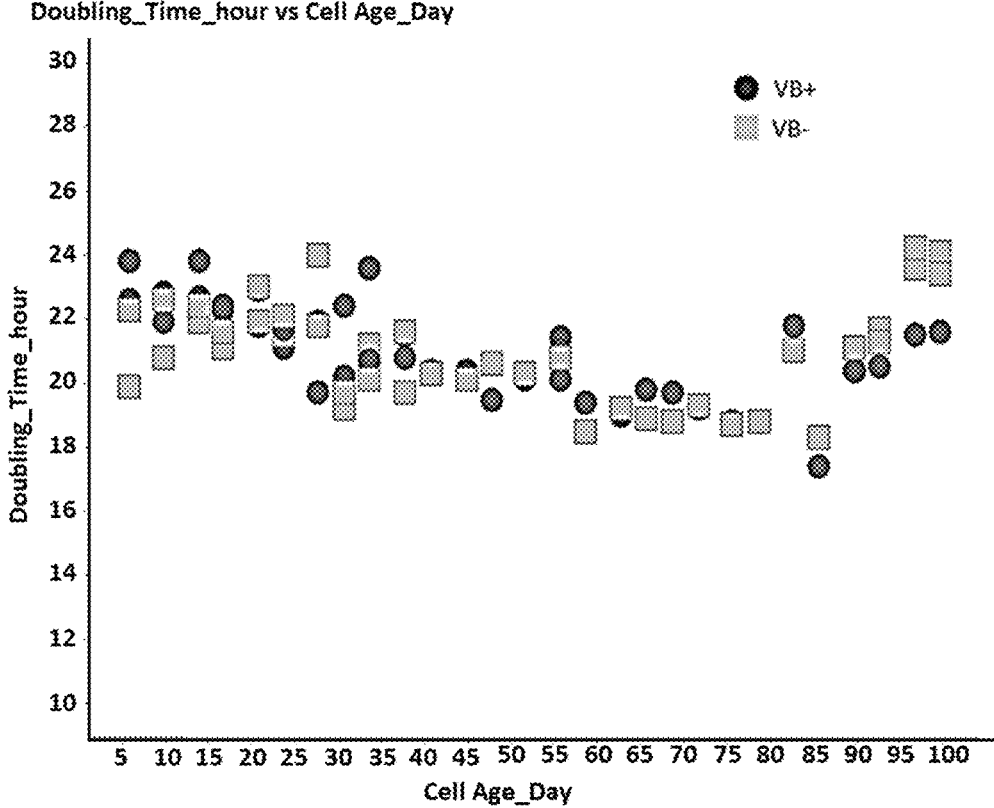
FIG. 4 shows the result of performing passage culture for up to 100 days (28 passages) on a three-day or four-day cycle and plotting a cell growth behavior on each day with the cell doubling time as an indicator, in culture of cells that produce antibody A, where VB+ is a culture medium containing VB12, and VB− is a culture medium free of VB12 (the measurement is performed with a cell automatic measuring apparatus Vi-CELL system (manufactured by Beckman Courter Inc.) and the cell doubling time is calculated).
Figure 5:
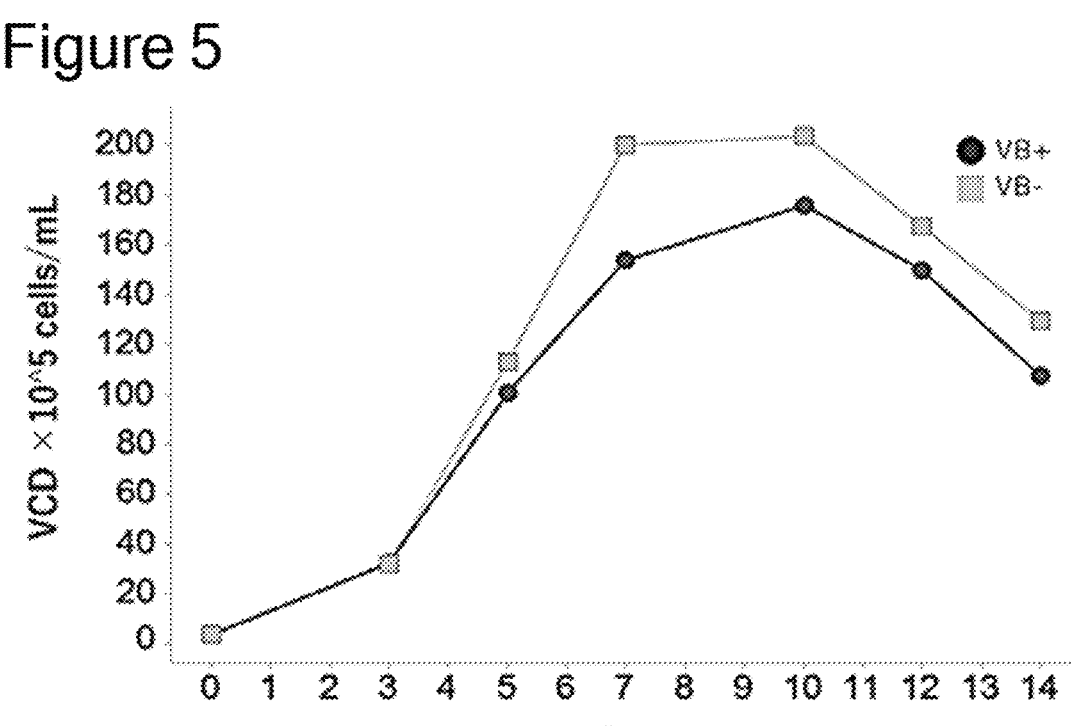
FIG. 5 shows the number of living cells measured on each of 14 culture days using a cell automatic measuring apparatus Vi-CELL system (manufactured by Beckman Courter Inc., Model: Vi-CELL XR) in culture of cells that produce a polypeptide (antibody B: anti-IL-8 antibody) different from that in FIG. 1, where VB+ is a culture medium having VB12 contained in an initial culture medium and a feed culture medium, and VB− is a culture medium having no VB12 contained in an initial culture medium and a feed culture medium.
Figure 6:
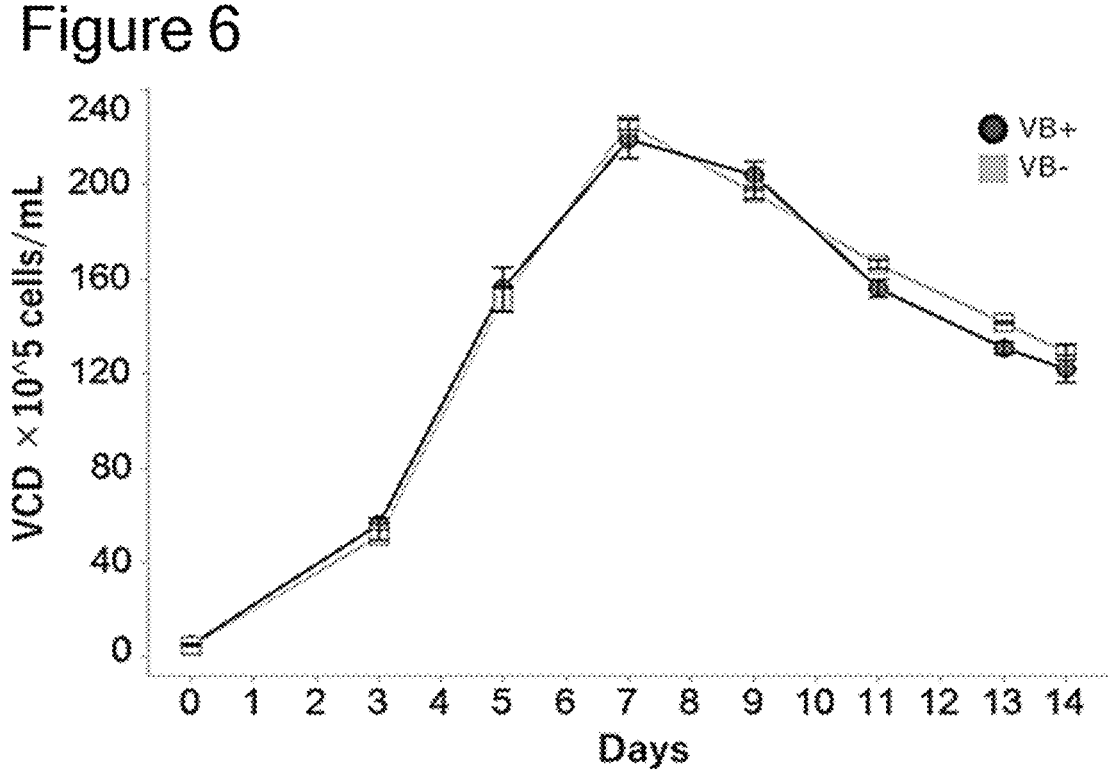
FIG. 6 shows the number of living cells measured on each of 14 culture days using a cell automatic measuring apparatus Vi-CELL system (manufactured by Beckman Courter Inc., Model: Vi-CELL XR) in culture of cells that produce a polypeptide (antibody C: anti-FIXa/FX dual-specificity antibody) different from that in FIGS. 1 and 5, where VB+ is a culture medium having VB12 contained in an initial culture medium and a feed culture medium, and VB− is a culture medium having no VB12 contained in an initial culture medium and a feed culture medium.
Figure 7:
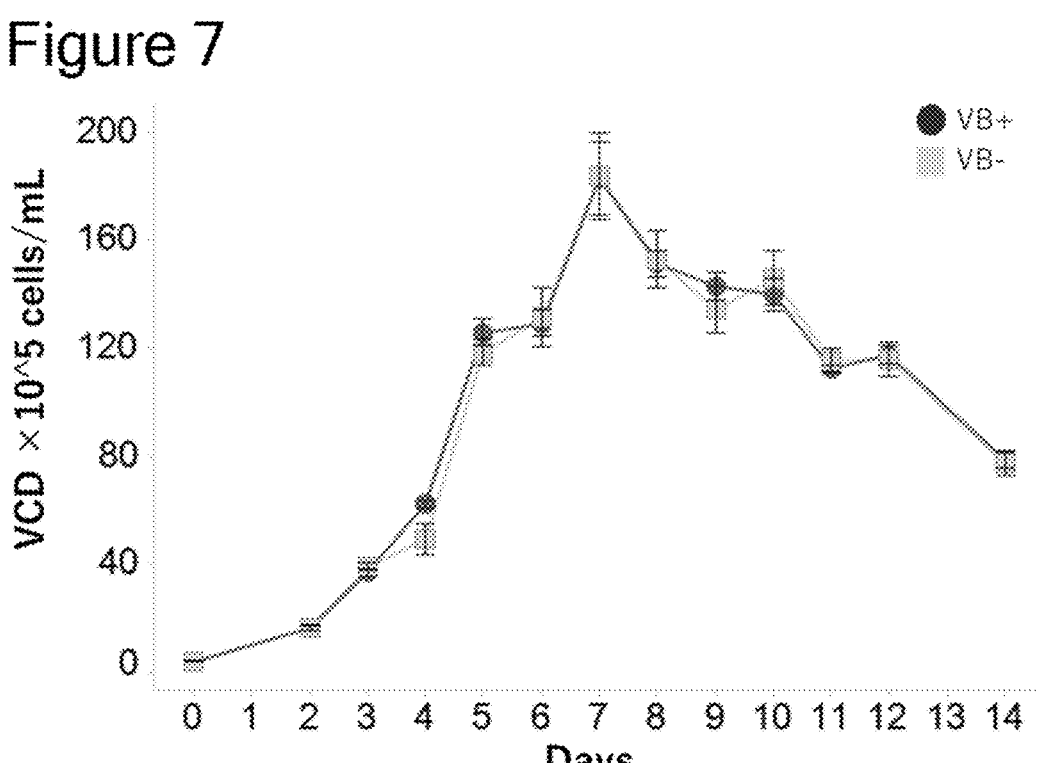
FIG. 7 shows the number of living cells measured on each of 14 culture days using a cell automatic measuring appa-

Effects of removal of VB12 from a culture medium for cell passage culture (manufactured by Thermo Fisher Scientific, Inc.) were observed. The results showed that passage culture with a culture medium (VB–) free of VB12 was substantially comparable in growth behavior to passage culture with a culture medium (VB+) containing VB12. It was confirmed that passage culture of cells producing antibody A was able to be performed for 100 days (28 passages) (FIG. 4), passage culture of cells producing antibody B was able to be performed for 136 days (39 passages) (FIG. 17) and passage culture of cells producing antibody C was able to be performed for 24 days (7 passages) (FIG. 18).

Example 6. Study on Possibility of Removing VB12 by Cation Exchange Chromatography Using an initial culture medium and a feed culture medium containing VB12, culture and affinity column chromatography treatment were performed in the same conditions as in Example 1. For the obtained antibody-containing composition, whether it was possible to remove VB12 by a cation exchange chromatography process, which is a binding/elute method, was examined. As in Example 1, the concentration of cobalt was measured by ICP-MS, and used as an indicator of the concentration of VB12.

The results showed that there was no change in cobalt/antibody [%] before passage through the CEX (cation exchange) and after elution from CEX (Table 4). Thus, it was confirmed that VB12 contained in the antibody-containing composition was not removed even when an additional chromatography process was applied.

TABLE 4

| | Cobalt/antibody [%] |
|---|---|
| Before passage through column | 0.29 |
| After elution | 0.31 |

Example 7. Additional Study on Effect of VB12 on Coloring of Antibody

Using a culture medium having VB12 contained in an initial culture medium and a feed culture medium, culture, affinity column chromatography treatment, a polishing process and concentration were performed in the same conditions as in Example 1. For the thus-obtained antibody-containing composition (antibody concentration: about 30 mg/ml, colored (slightly red)), an additional study was conducted on adsorption of VB12 to the antibody.

Potassium cyanide was added to the antibody-containing composition at 0.1% (as a control, a test was also conducted under a condition without the addition of potassium cyanide), and the resulting mixture was held at 37° C. for 45 minutes. These samples were caused to pass through a 5 KD cutoff filter, and collected samples from which the antibody had been removed were analyzed by reversed phase chromatography. The results showed that the potassium cyanide-non-treated sample (KCN–) did not have a peak for VB12 (cyanocobalamin), whereas the potassium cyanide-treated sample (KCN+) had a peak indicating VB12 (cyanocobalamine) (FIG. 19, antibody A). The results showed that VB12 was released from the antibody by the treatment with potassium cyanide, and it was confirmed that VB12 had an effect on coloring of the antibody.

INDUSTRIAL APPLICABILITY

The present invention can be used for production of a medicament containing a polypeptide.

The invention claimed is:

1. A method for producing a composition containing a polypeptide with suppressed coloring, wherein the polypeptide is a Fc-containing polypeptide, the method comprising the steps of:
   a) culturing CHO cells containing a nucleic acid encoding the Fc-containing polypeptide by fed-batch culture in a cell culture medium, wherein the fed-batch culture is performed with an initial culture medium and a feed culture medium wherein the concentration of cobalt molecules contained in vitamin B12 in both culture media is less than 20 ppb; and
   b) collecting a composition containing the polypeptide from the culture.

2. The method for producing a composition according to claim 1, wherein the molar concentration ratio of vitamin B12 to the polypeptide in the collected composition is less than 0.26%.

3. The method for producing a composition according to claim 1, wherein the viable cell density (VCD) in the cell culture medium on the seventh day after the start of the fed-batch culture is $80 \times 10^5$ cells/mL or more.

4. The method for producing a composition according to claim 1, wherein the Fc-containing polypeptide is an antibody.

5. The method for producing a composition according to claim 1, wherein the polypeptide contains a modification of at least one amino acid residue selected from amino acid residues at positions 214, 234, 238, 250, 264, 307, 311, 330, 343, 428, 434, 436, 438 and 440 according to EU numbering in the Fc region.

6. The method for producing a composition according to claim 1, wherein the polypeptide contains a modification of at least one selected from 214R, 234Y, 238D, 250V, 264I, 307P, 311R, 330K, 343R, 428L, 434A, 436T, 438R and 440E according to EU numbering in the Fc region.

7. The method for producing a composition according to claim 1, wherein the polypeptide is an antibody comprising a heavy chain constant region containing an amino acid sequence of SEQ ID NO: 1 and a light chain constant region containing an amino acid sequence of SEQ ID NO: 2.

8. The method for producing a composition according to claim 7, wherein the antibody is a humanized IgG1 antibody which binds to latent myostatin.

9. A method for producing a composition containing an antibody with suppressed coloring, the method comprising the steps of:
   a) identifying an antibody of interest as an antibody containing a modification of at least one amino acid residue selected from amino acid residues at positions 214, 234, 238, 250, 264, 307, 311, 330, 343, 428, 434, 436, 438 and 440 according to EU numbering in the Fc region;
   b) selecting a cell culture medium for the antibody containing a modification of the amino acid residue, wherein the concentration of cobalt molecules contained in vitamin B12 in the culture medium is less than 20 ppb;
   c) culturing CHO cells containing a nucleic acid encoding the antibody containing a modification of the amino acid residue in the cell culture medium selected in step b) by fed-batch culture; and
   d) collecting a composition containing the antibody from the culture.

10. The method for producing a composition according to claim 9, wherein an initial culture medium free of vitamin B12 and a feed culture medium free of vitamin B12 are selected in step b).

11. The method for producing a composition according to claim 4, wherein the antibody contains a modification of at least one amino acid residue selected from amino acid residues at positions 214, 234, 238, 250, 264, 307, 311, 330, 343, 428, 434, 436, 438 and 440 according to EU numbering in the Fc region.

12. The method for producing a composition according to claim 4, wherein the antibody contains a modification of at least one selected from 214R, 234Y, 238D, 250V, 264I, 307P, 311R, 330K, 343R, 428L, 434A, 436T, 438R and 440E according to EU numbering in the Fc region.

13. The method for producing a composition according to claim 5, wherein the polypeptide contains a modification of at least one selected from 214R, 234Y, 238D, 250V, 264I, 307P, 311R, 330K, 343R, 428L, 434A, 436T, 438R and 440E according to EU numbering in the Fc region.

14. The method for producing a composition according to claim 11, wherein the antibody contains a modification of at least one selected from 214R, 234Y, 238D, 250V, 264I, 307P, 311R, 330K, 343R, 428L, 434A, 436T, 438R and 440E according to EU numbering in the Fc region.

15. The method for producing a composition according to claim 11, wherein the antibody is a humanized IgG1 antibody which binds to latent myostatin.

16. The method for producing a composition according to claim 12, wherein the antibody is a humanized IgG1 antibody which binds to latent myostatin.

17. The method for producing a composition according to claim 14, wherein the antibody is a humanized IgG1 antibody which binds to latent myostatin.

\* \* \* \* \*

SEQUENCE LISTING

<160> NUMBER OF SEQ ID NOS: 2

<210> SEQ ID NO 1
<211> LENGTH: 328

```
<212> TYPE: PRT
<213> ORGANISM: Artificial sequence
<220> FEATURE:
<223> OTHER INFORMATION: An artificially synthesized sequence

<400> SEQUENCE: 1

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Tyr Leu Gly Gly Asp Ser Val Phe Leu Phe Pro Pro
        115                 120                 125

Lys Pro Lys Asp Val Leu Met Ile Ser Arg Thr Pro Glu Val Thr Cys
    130                 135                 140

Val Val Ile Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Pro Val Leu
            180                 185                 190

His Arg Asp Trp Leu Asn Gly Lys Glu Tyr Lys Cys Lys Val Ser Asn
        195                 200                 205

Lys Ala Leu Pro Lys Pro Ile Glu Lys Thr Ile Ser Lys Ala Lys Gly
    210                 215                 220

Gln Arg Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Leu His Glu Ala Leu His Ala His Thr Thr
305                 310                 315                 320

Arg Lys Glu Leu Ser Leu Ser Pro
                325

<210> SEQ ID NO 2
<211> LENGTH: 107
<212> TYPE: PRT
<213> ORGANISM: Artificial sequence
<220> FEATURE:
<223> OTHER INFORMATION: An artificially synthesized sequence
```

-continued

```
<400> SEQUENCE: 2

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```